(12) United States Patent
Kaizuka

(10) Patent No.: US 6,432,387 B1
(45) Date of Patent: Aug. 13, 2002

(54) IONIC TOOTH POLISHING AGENT

(75) Inventor: Kazutoshi Kaizuka, Fukuoka (JP)

(73) Assignee: Create Co., Ltd., Fukuoka (JP)

( * ) Notice: Subject to any disclaimer, the term of this patent is extended or adjusted under 35 U.S.C. 154(b) by 0 days.

(21) Appl. No.: 09/536,001

(22) Filed: Mar. 23, 2000

(51) Int. Cl.⁷ .............................. A61K 7/16; A61K 7/18
(52) U.S. Cl. ........................................... 424/49; 424/52
(58) Field of Search ..................... 424/49, 52

(56) References Cited

U.S. PATENT DOCUMENTS

| | | | | |
|---|---|---|---|---|
| 3,228,845 A | * | 1/1966 | Najjar | 167/93 |
| 4,143,126 A | * | 3/1979 | Gaffar | 424/49 |
| 5,124,143 A | * | 6/1992 | Muhlemann et al. | 424/49 |
| 5,266,304 A | * | 11/1993 | Bafelli et al. | 424/49 |
| 5,891,473 A | * | 4/1999 | Stanier | 424/489 |

* cited by examiner

*Primary Examiner*—Frederick Krass
*Assistant Examiner*—Donna Jagoe
(74) *Attorney, Agent, or Firm*—Dave B. Koo; Squire, Sanders & Dempsey L.L.P.

(57) ABSTRACT

A tooth polishing agent for effectively removing stains such as tobacco tar and tartar with the use of a toothbrush and gentle brushing, using only a small amount of the tooth polishing agent. The improved tooth polishing agent of the present invention generates negative ions in the mouth, effectively cleaning the teeth without the use of large amounts of abrasives or aggressive brushing. The negative ions also act to improve circulation of the blood in the gums and prevent gum disease. The tooth polishing agent of the present invention is constituted with the powdered form of a multi-element mineral, which negatively ionizes water. This multi-element mineral contains a balance of elements, including silica-like perlite, pitchstone and tourmaline.

3 Claims, No Drawings

IONIC TOOTH POLISHING AGENT

BACKGROUND OF THE INVENTION

1. Field of the Invention

The present invention relates generally to dental hygienic products, and more particularly to an improved tooth polishing agent.

2. Description of Related Art

Tooth polishing agents, including toothpastes and gels, are well known in the art. Most such agents containing blended ingredients such as an abrasive, a lubricant, a foaming agent, a caking additive, a flavor additive, medicine and water are generally known. The main ingredient in many tooth polishing agents is an abrasive, which is used to remove tartar and other stains caused by food, tobacco, coffee, etc. By removing these staining items from the teeth, the abrasive ingredient generally imparts brilliance to the teeth. However, the use of abrasive does not come without a cost. Many times, when the removal of particularly stubborn stains is difficult, large amounts of a tooth polishing agent combined with aggressive brushing is necessary. This action on a regular basis causes the surface of the teeth, and in some cases the enamel, to be removed, creating various problems with the teeth and gums.

Thus, there exists a need to provide a tooth polishing agent that can be used in small amounts, requiring only light brushing, which will just as effectively remove the stubborn stains caused by tobacco tar and the like, without removing the surface of the tooth.

SUMMARY OF THE INVENTION

Accordingly, the present invention provides an improved tooth polishing agent that generates negative ions in the mouth, effectively cleaning the teeth without the use of large amounts of abrasives or aggressive brushing. The tooth polishing agent of the present invention is constituted with the powdered form of a multi-element mineral, which releases negative ions when hydrated. The ions may contribute to remineralization of the enamel as well as cleaning the teeth. The multi-element mineral of the present invention contains a balance of elements, including silica-like perlite, pitchstone and tourmaline.

These and other features and advantages of the present invention will become more apparent to those skilled in the art when taken with reference to the following more detailed description of the preferred embodiments of the invention.

BRIEF DESCRIPTION OF THE DRAWINGS

Not Applicable

DETAILED DESCRIPTION OF THE PREFERRED EMBODIMENTS

The present invention satisfies the need for improved tooth polishing agents. More particularly, the present invention provides tooth polishing agents that are characterized by the inclusion of a multi-element mineral that produces negative ions.

When the tooth polishing agent of the present invention is used to polish ones teeth, negative ions are produced from the powdered form of the multi-element mineral contained therein. Consequently, by means of the action of the negative ions when polishing the teeth with a toothbrush, a cluster phenomenon is produced in the water, making the water molecule groups smaller. The water in the mouth is therefore refined and the dissolving power possessed by the water is improved. This facilitates the removal of stains such as tartar and tobacco tar that are adhering to the teeth because the positive ions contained therein are effectively counteracted. Therefore, even a small amount of the tooth polishing agent of the present invention combined with gentle brushing effectively removes stains without injury to the teeth. Negative ions may contribute to remineralization of the teeth. Furthermore, the negative ions can activate cells in the gums, improving circulation of the blood in the gums, which aids in preventing gum disease.

The tooth polishing agent of the present invention contains several ingredients found in prior art toothpastes in addition to the inventive multi-element mineral. A light abrasive for aiding in removing tartar and tar is included, made up of compounds such as silicic acid anhydride, secondary calcium phosphate and calcium carbonate. A lubricant to impart moisture is also included, made up of elements such as glycerol and sorbitol. A foaming agent such as sodium laurate is used to cause the tooth polishing agent to be diffused inside the mouth. A viscosity increasing agent, made up of materials such as sodium alginate and carboxymethylcellulose (CMC), is used so that the powder and liquid do not separate within the tooth polishing agent. A flavor additive, made up of materials such as peppermint, mentha arvensis (peppermint oil) and synthetic flavors, is used to impart a refreshing feeling to the inside of the mouth. Medicine is used to prevent cavities and gum disease, including fluoride, a fermentation agent, a disinfectant and an astringent. Finally, water is used as a dissolving agent to impart moisture to the tooth polishing agent.

The multi-element mineral of the present invention is a mineral that contains a balance of elements, including silica-like perlite, pitchstone and tourmaline. The composition of one form of perlite is given below in table 1 as an example of a multi-element mineral of the present invention.

TABLE 1

| PERLITE ELEMENT | AMOUNT (%) |
|---|---|
| Silicon Dioxide ($SiO_2$) | 71.94 |
| Aluminum Oxide ($Al_2O_3$) | 14.94 |
| Alkali Oxide ($K_2O + Na_2O$) | 6.87 |
| Iron Oxide ($Fe_2O_3$) | 2.54 |
| Calcium Oxide (CaO) | 2.47 |
| Magnesium Oxide (MgO) | 0.44 |
| Phosphoric Anhydride ($P_2O_5$) | 0.14 |
| Manganese Oxide (MnO) | 0.03 |
| Other (Ti) | Trace |
| Loss on Ignition | 0.63 |

The chemical formula of tourmaline (the general name of a tourmaline group mineral, which is a trigonal system) is given below:

$$AB_3C_6 [(OH, F, O)_4 | (BO_3) | Si_6O_{18}]$$

Where
A=Na or Ca
B=Mg or Fe (II) or Mn (II) or Al (V)
C=Al or Fe (III) or Cr (III)

The most common combination of elements for tourmaline are found in:

Dravite A=Na, B=Mg, C=Al)

Schorl (A=Na, B=Fe (III), C=Al)

The multi-element mineral is pulverized in a ball mill, or the like, down to a size of 0.5–3.0 microns, preferably 0.5–1.0 microns, forming a powder. It is desirable that two types of the powdered form be blended before inserting into the tooth polishing agent of the present invention, although one type is acceptable. The tooth polishing agent of the present invention contains 0.2% to 0.5% of the multi-element mineral in the preferred embodiment. The multi-element mineral can be combined with water before inserting into the tooth polishing agent. This is accomplished by mixing the powdered form of a multi-element mineral with water by heat or pressure to mix in the supernant liquid. The mixture can also be vacuum freeze dried or spray dried to produce a powder after mixing.

Many alterations and modifications may be made by those having ordinary skill in the art without departing from the spirit and scope of the present invention. For example, a tooth polishing agent has been illustrated with many exemplary ingredients. It should be apparent, however, that the inventive concepts described above would be equally applicable to other ingredients including salt grains and hydroxyapatite. Moreover, the words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself The definitions of the words or elements of the following claims are, therefore, defined in this specification to include not only the combination of elements which are literally set forth, but all equivalent structure, material or acts for performing substantially the same function in substantially the same way to obtain substantially the same result.

I claim:

1. A tooth polishing agent comprising:

a light abrasive;

a lubricant;

a foaming agent;

a viscosity increasing agent;

a flavor additive;

medicine;

water; and a multi-element mineral powder containing a balance of elements, which releases negative ions when hydrated, said negative ions facilitating removal of stains and improving circulation of the blood in the gums, wherein the amount of the multi-element mineral powder added to said agent is between 0.2% and 0.5% by weight.

2. The tooth polishing agent of claim 1, wherein the multi-element mineral power is silica-like perlite.

3. The tooth polishing agent of claim 1, wherein the multi-element mineral powder is combined with water prior to addition to said agent.

* * * * *